United States Patent
Daram

(10) Patent No.: US 6,422,243 B1
(45) Date of Patent: Jul. 23, 2002

(54) TASTE BUD SHIELD AND METHOD OF USING SAME

(76) Inventor: Sarojini Daram, 221 11th Ave. East, Floodwood, MN (US) 55736

( * ) Notice: Subject to any disclaimer, the term of this patent is extended or adjusted under 35 U.S.C. 154(b) by 0 days.

(21) Appl. No.: 09/735,068

(22) Filed: Dec. 11, 2000

(51) Int. Cl.[7] .................................................. A61C 5/14
(52) U.S. Cl. ...................................... 128/859; 128/860
(58) Field of Search .................................. 128/848, 859, 128/860, 861, 862; 433/6, 215, 229; 602/902

(56) References Cited

U.S. PATENT DOCUMENTS

| | | | |
|---|---|---|---|
| 1,365,684 A | * 1/1921 | Guise | 128/860 |
| 1,405,689 A | * 2/1922 | Huntwole | 128/860 |
| 3,312,216 A | * 4/1967 | Wallshein | 128/860 |
| 3,818,906 A | 6/1974 | Stubbs | |
| 4,471,771 A | 9/1984 | Brown et al. | |
| 4,738,259 A | 4/1988 | Brown et al. | |
| D296,359 S | 6/1988 | Dixon | |
| 4,976,275 A | * 12/1990 | Dixon | 128/860 |
| 5,236,415 A | 8/1993 | Stallings | |
| 5,373,859 A | * 12/1994 | Forney | 128/860 |
| 5,507,278 A | 4/1996 | Karell | |
| 5,692,493 A | 12/1997 | Weinstein et al. | |
| 5,924,422 A | 7/1999 | Gustafson | |
| 5,979,449 A | 11/1999 | Steer | |

* cited by examiner

*Primary Examiner*—Michael A. Brown
(74) *Attorney, Agent, or Firm*—Meroni & Meroni, P.C.; Charles F. Meroni, Jr.

(57) ABSTRACT

A taste bud shield for preventing contact between food stuff and taste buds on a tongue including a form fitting protective sheath extending the apex to the root of the tongue completely covering the dorsal surface to at least the terminal sulcus, the ventral surface to at least the frenulum, and the side surfaces. The sheath has an inner and outer surface, the inner surface of the sheath directly overlaying the fungiform, foliate and circumvallate papillae, and at least one sheath fastener on either side and extending outwardly from the outer surface of the sheath adjacent the molars. A programmable mating fastener is affixed to at least one molar on either side of the sheath and adjacent the sheath fasteners for removably coupling with same for a predetermined period of time.

21 Claims, 3 Drawing Sheets

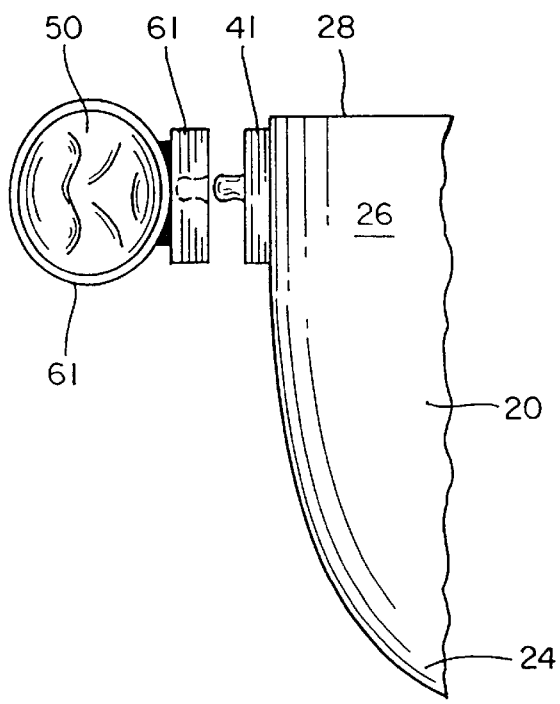
_Fig. 5_
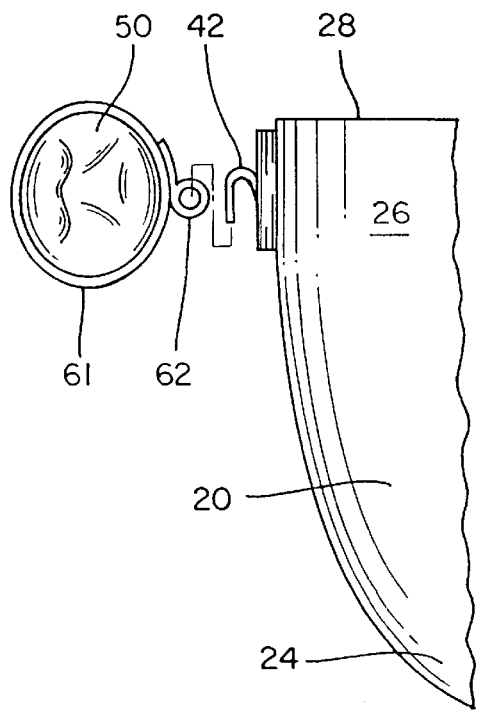
_Fig. 6_
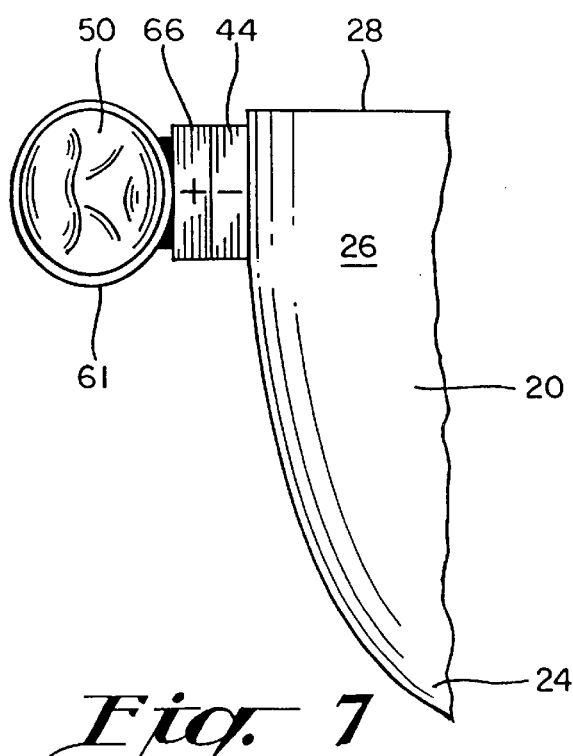
_Fig. 7_

TASTE BUD SHIELD AND METHOD OF USING SAME

FIELD OF THE INVENTION

The present invention relates to an apparatus and method of using same for weight reduction, and, more particularly, to a form fitting, flexible, impermeable, and bio-compatible taste bud shield for preventing food stuff from contacting the taste buds of the tongue thereby rendering the food stuff tasteless and unpalatable, and method of using same.

BACKGROUND OF THE INVENTION

Various devices have been used in the past for weight reduction. Unfortunately, these devices have many drawbacks reducing their efficacy. For example, U.S. Pat. No. 4,471,771 issued to Steven et al. and entitled "Oral Weight Control Device" discloses a sieve like guard pivotally coupled to an upper support member adapted to be secured to the inside back of the user's mouth. The guard raises and lowers in response to movements of the user's tongue, and has meshed openings of a selected size to impede the passage of large food particles when swallowing. What is intended is a reduction in the rate of food consumption, and to allow the body to naturally register the sensation of being full prior to the completion of a meal. The device, however, seems awkward and uncomfortable to use, and may prove to be a choking hazard. Furthermore, if a user grinds food to fine particles as a natural course of his mastication process, then the rate of consumption will not be reduced at all because the mesh will not impede the swallowing of food particles.

U.S. Pat. No. 4,738,259 issued to Brown et al. and entitled "Dental Appliance For Weight Control" discloses a device for attachment to a user's teeth for interfering with natural mastication and transport of food within the user's mouth to impede the rate of food consumption, and, in turn, cause weight reduction. The device is positioned between opposing chewing surfaces of teeth within the user's mouth. In this manner, the device impedes transfer of food and access of the user's tongue to the chewing region between the opposing teeth. Again, such a device seems awkward and uncomfortable to use, and long term use of such a device does not seem probable.

Another weight control apparatus disclosed in U.S. Pat. No. 5,924,422 issued to Gustafson and entitled "Oral Device To Aid Weight Control" is a device having a molded element positioned against the roof of a user's mouth to temporarily alter the configuration of the palate whereby the food-containing volume of the mouth is reduced and the quantity of food per bite is reduced. This device, however, may affect the mastication process in that it restricts the movement of the tongue.

Therefore, it is an object of the present invention to provide a device and method of using same for weight reduction that is comfortable and easy to use.

It is another object of the present invention to provide a device and method of using same that does not interfere with the mastication process, nor presents a choking hazard.

It is yet another object of the present invention to provide a device and method of use for preventing contact between food stuff and a user's taste buds so that the food stuff is rendered tasteless and unpalatable resulting in less consumption of same by the user.

Other objects and features will become readily apparent when the disclosure is read in combination with the drawings and appended claims.

SUMMARY OF THE INVENTION

What is disclosed is a taste bud shield for preventing contact between food stuff and taste buds on a tongue comprising, a form fitting protective sheath having an inner and outer surface extending the apex to the root of the tongue completely covering the dorsal surface to at least the terminal sulcus, the ventral surface to at least the frenulum, and the side surfaces, the inner surface of the sheath directly overlaying the fungiform, foliate and circumvallate papillae, a sheath fastener on either side and extending outwardly from the outer surface of the sheath adjacent the molars, and a mating fastener affixed to at least one molar on either side of the sheath and adjacent the sheath fasteners for removably coupling with same within the oral cavity.

The protective sheath is comprised of a flexible impermeable biocompatible material. In one embodiment, protective sheath is comprised of rubber. It is contemplated, however, that the sheath may be constructed from other materials such as plastic and the like.

The mating fasteners are removably affixed to the crown of at least one molar on either side of the sheath. In one embodiment, the mating fasteners further comprises a programmable locking mechanism to couple with the sheath fasteners and anchor the taste bud shield within the oral cavity for a predetermined period of time.

The sheath fasteners may be integrally formed with the sheath. In the preferred embodiment, the mating fasteners further comprise a programmable locking mechanism to couple with the sheath fasteners and anchor the taste bud shield within the oral cavity for a predetermined period of time. In another embodiment, the sheath fasteners comprise hooks and the mating fasteners comprise loops, the hooks and loops configured to removably couple with one another to anchor the sheath within the oral cavity. In yet another embodiment, the sheath fasteners comprise snap buttons and the mating fasteners comprise mating snap buttons removably anchoring the sheath within the oral cavity by snap-fit engagement with one another. In still another embodiment, the sheath and mating fasteners comprise magnets of opposite polarity attracting and coupling with one another to anchor the sheath within the oral cavity.

What is also disclosed is a method of preventing contact between food stuff and taste buds on a tongue comprising the steps of shielding the taste buds on a tongue with a form fitting protective sheath extending from the apex to the root of the tongue completely covering the dorsal surface to at least the terminal sulcus, the ventral surface to at least the frenulum, and the side surfaces, the sheath having an inner and outer surface, the inner surface of the sheath directly overlaying the fungiform, foliate and circumvallate papillae, and at least one sheath fastener on either side and extending outwardly from the outer surface of the sheath adjacent the molars of the lower jaw, and anchoring the protective sheath within the oral cavity.

The step of anchoring the protective sheath within the oral cavity may further comprise the steps of affixing mating fasteners to at least one molar on either side of the sheath and adjacent the sheath fasteners, and coupling the mating fasteners to the respective sheath fasteners.

BRIEF DESCRIPTION OF THE DRAWINGS

The invention is illustrated in the figures of the accompanying drawings which are meant to be exemplary and not limiting, in which like references refer to like or corresponding parts, and in which:

FIG. 5 is a partial top plan view of another embodiment of the taste bud shield of the present invention;

FIG. 6 is a partial top plan view of yet another embodiment of the taste bud shield of the present invention; and FIG. 7 is a partial top plan view of still another embodiment of the taste bud shield of the present invention.

DETAILED DESCRIPTION OF THE INVENTION

Figure 1:
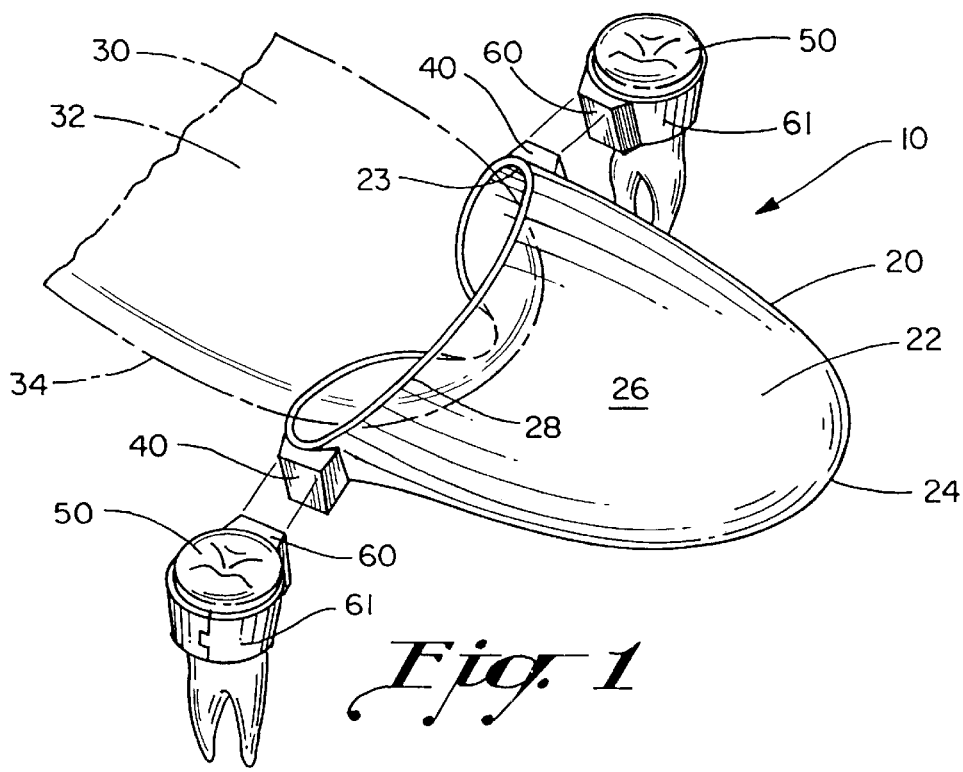
FIG. 1 is an exploded perspective view of taste bud shield of the present invention.
Figure 2:
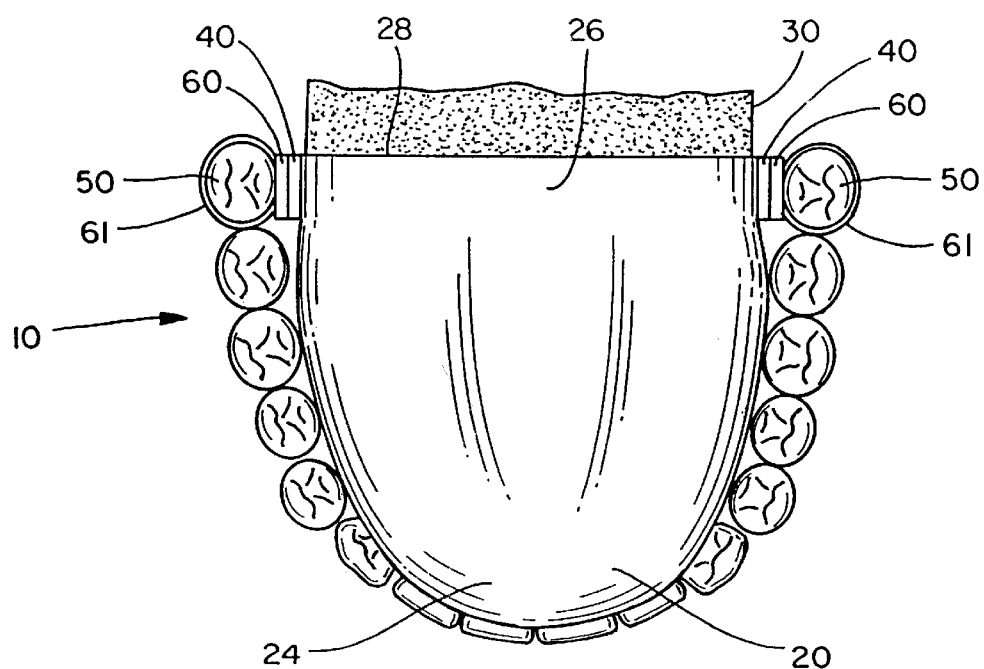
FIG. 2 is a top plan view of the taste bud shield.
Figure 3:
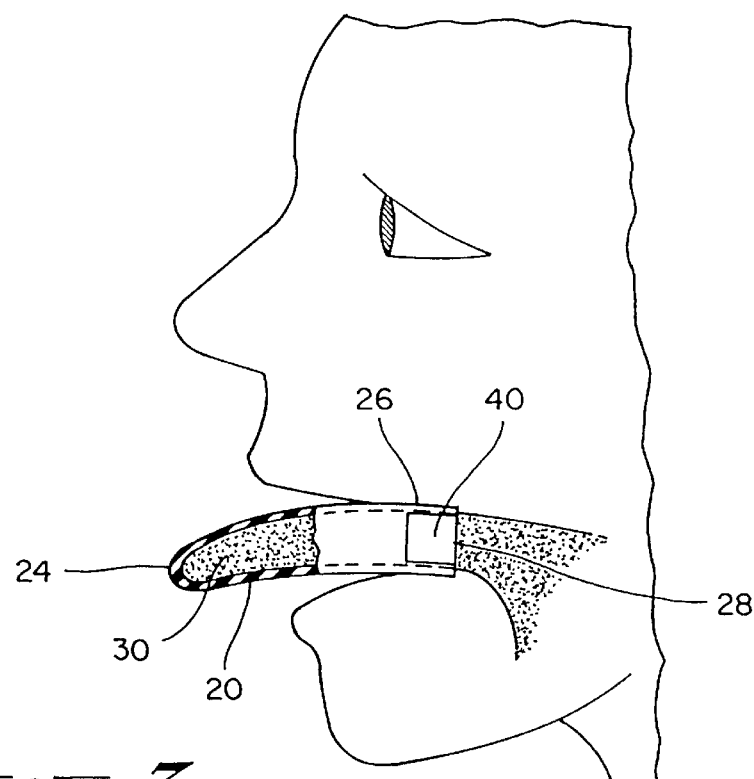
FIG. 3 is a side view of the taste bud shield of the present invention.

Turning now to the drawings, and more particularly, to FIGS. 1–3, a taste bud shield is shown generally at 10. Taste bud shield 10 is comprised of a stretchable form fitting sheath 20 comprised of a flexible, impermeable, and biocompatible material that does not interfere with the natural movements of the tongue. In the preferred embodiment, the sheath is comprised of rubber. It is contemplated, however, that sheath 20 may be comprised of plastic and the like. Also, sheath 20 may have a uniform or variable thickness. For example, sheath 20 may have a greater thickness at the fungiform, foliate and circumvallate papillae regions to ensure that food stuff does not contact the taste buds in those regions. Outer surface 22 of sheath 20 may be smooth or textured depending on the user's preference. Furthermore, sheath 20 may either be disposable or reusable.

The apex region 24 of sheath 20 is closed and tapers up to the root region 26 which is open to provide access for a tongue that is to be shielded from food stuff. The root end 28 of sheath 20 extends past the terminal sulcus 32 of tongue 30 on the dorsal surface, the foliate papillae of the sides 34, and up to the frenulum (not shown) on the ventral surface. In the preferred embodiment, sheath 20 extends beyond the frenulum on either side along the ventral surface.

Sheath fasteners 40 extend outwardly from outer surface 22 at the root region 26 of sheath 20 adjacent the molars 50. Sheath fasteners 40 may be integrally formed with sheath 20, or may later be affixed thereto.

Mating fasteners 60 are removably affixed to molars 50 and are configured to couple with sheath fasteners 40 to anchor sheath 20 within the oral cavity. In one embodiment, mating fasteners 60 are banded by bands 61 about the crown of at least one molar of the lower jaw on either side of sheath 20 and positioned so as not to interfere with the mastication process. It is contemplated, however, that mating fasteners 60 may be secured to a plurality of molars on either side of sheath 20.

Figure 4:
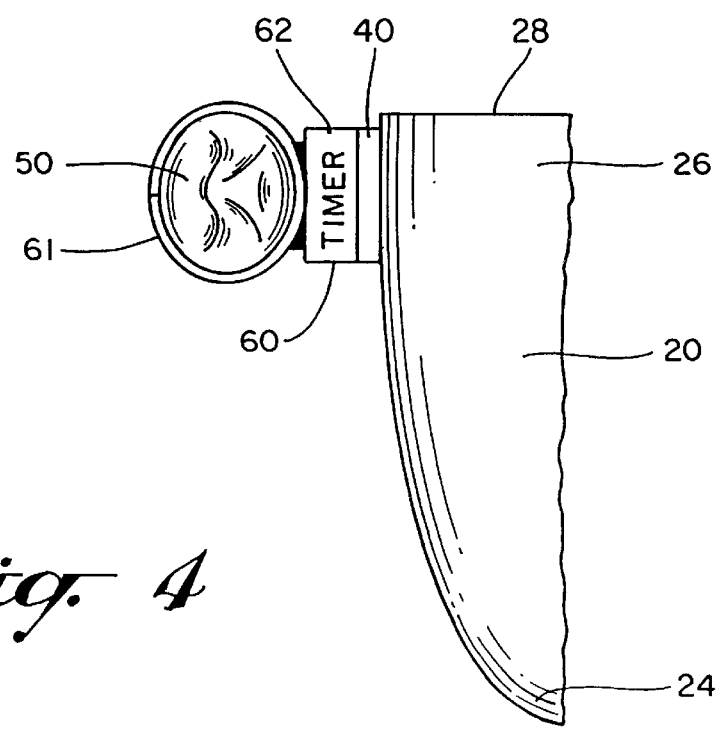
FIG. 4 is a partial top plan view of one embodiment of the taste bud shield of the present invention.

In the preferred embodiment, as shown in FIG. 4, mating fasteners 60 are associated with a timer mechanism 62 that is programmable. In this manner, mating fasteners 60 can couple with sheath fasteners 40 for a predetermined period of time.

In another embodiment, shown in FIG. 5, the sheath fasteners 40 and the mating fasteners 60 are snap buttons 41 and 61 that removably anchor sheath 20 within the oral cavity by snap-fit engagement with one another.

In FIG. 6, what is shown is a hook and loop mechanism for anchoring sheath 20 within the oral cavity. Sheath fasteners 40 comprise hooks 42 and mating fasteners 60 comprise loops 62. Hooks 42 and loops 62 are configured to removably couple with one another.

In yet another embodiment, sheath fasteners 40 and mating fasteners 60 comprise magnets 44, 66 of opposite polarity attracting and coupling with one another. The magnets are of sufficient strength so as not to uncouple during mastication.

While certain embodiments have been described and illustrated for anchoring the sheath within the oral cavity, it must be understood that other methods can also be used to achieve the same results. Such other methods may include anchoring the sheath to the molars by rubber bands and the like.

In operation, mating fasteners 60 are banded about the crown of at least one molar on either side of the lower jaw. A dentist, oral surgeon or physician may perform this procedure. In the preferred embodiment, the mating fasteners have a programmable timer mechanism 62 to couple with sheath fasteners 40 for a predetermined period of time. A period of time is programmed into the timer mechanism 62, and the mating fasteners are then affixed to the molars. The programmable mating fasteners may, however, be programmed after affixing them to the molars.

Sheath 20 is then placed within the oral cavity and over the tongue of a patient. The tongue is inserted into sheath 20 from the opening provided at the root end 28 of the sheath. The tip of the tongue rests against the closed apex end 24 inside of the sheath. The inner surface 23 of sheath 20 directly overlies the fungiform, foliate and circumvallate papillae preventing contact between foodstuff and the taste buds. Sheath fasteners 40 are then coupled to mating fasteners 60 to anchor the sheath in place for a set period of time.

When the patient feels hunger and consumes foodstuff, the sense of taste is inhibited. Because of the tasteless nature of the food, the patient will find the foodstuff to be unpalatable and will either reduce or avoid consumption of same. In this manner, the patient will intake less calories. The fewer calories consumed, the more the body will have to burn stored calories. Ultimately, there will be a reduction in body weight.

When the set period of time has been reached, the timer mechanism uncouples the mating fasteners from the sheath fasteners, and the sheath may be removed from the oral cavity for sanitizing or disposal.

Where the sheath and mating fasteners comprise snap buttons as shown in FIG. 5, hooks and loops as shown in FIG. 6, or magnets as shown in FIG. 7, the sheath may be anchored or released as desired by a patient. In these embodiments, the patient may where the tongue shield whenever there is a sense of hunger. Again, when the patient eats, the foodstuff is unpalatable and tasteless causing the patient to consume less. This will ultimately result in weight reduction for the patient.

As various possible embodiments may be made in the above invention for use for different purposes and as various changes might be made in the embodiments and methods above set forth, it is understood that all of the above matters here set forth or shown in the accompanying drawings are to be interpreted as illustrative and not in a limiting sense.

What is claimed is:

1. A taste bud shield for preventing contact between food stuff and taste buds on a tongue comprising:

a form fitting sheath having an inner and outer surface extending from the apex to the root of the tongue completely covering the dorsal surface to at least the terminal sulcus, the ventral surface to at least the frenulum, and the side surfaces, the inner surface of the sheath directly overlaying the fungiform, foliate and circumvallate papillae;

a sheath fastener on either side and extending outwardly from the outer surface of the sheath adjacent the molars; and a mating fastener adapted to be affixed to at least one molar on either side of the sheath and adjacent the sheath fasteners for removably coupling with same to anchor the sheath within the oral cavity.

2. The taste bud shield of claim 1, wherein the sheath is comprised of a flexible impermeable biocompatible material.

3. The taste bud shield of claim 2, wherein the flexible impermeable biocompatible material is rubber.

4. The taste bud shield of claim 3, wherein the mating fastener is adapted to be removably affixed to the crown of at least one molar on either side of the sheath.

5. The taste bud shield of claim 4, wherein the mating fasteners further comprise a programmable locking mechanism to couple with the sheath fasteners and anchor the taste bud shield within the oral cavity for a predetermined period of time.

6. The taste bud shield of claim 5, wherein the sheath fasteners are integrally formed with the sheath.

7. The taste bud shield of claim 6, wherein the form fitting sheath is disposable.

8. The taste bud shield of claim 7, wherein the form fitting sheath is reusable.

9. The taste bud shield of claim 3, wherein the mating fastener adapted to be is affixed to a plurality of molars of the lower jaw on either side of the sheath and adjacent the sheath fasteners for removably anchoring the sheath within the oral cavity.

10. The taste bud shield of claim 3, wherein the sheath and mating fasteners comprise magnets of opposite polarity attracting and coupling with one another to anchor the sheath within the oral cavity.

11. The taste bud shield of claim 3, wherein the sheath fasteners comprise hooks and the mating fasteners comprise loops, the hooks and loops configured to removably couple with one another to anchor the sheath within the oral cavity.

12. The taste bud shield of claim 3, wherein the sheath fasteners comprise snap buttons and the mating fasteners comprise mating snap buttons removably anchoring the sheath within the oral cavity by snap-fit engagement with one another.

13. A taste bud shield for preventing contact between food stuff and taste buds on a tongue comprising:

a form fitting flexible impermeable bio-compatible protective sheath having an inner and outer surface extending the apex to the root of the tongue completely covering the dorsal surface to at least the terminal sulcus, the ventral surface to at least the frenulum, and the side surfaces, the inner surface of the sheath directly overlaying the fungiform, foliate and circumvallate papillae;

at least one sheath fastener on either side and extending outwardly from the outer surface of the sheath adjacent the molars; and at least one mating fastener adapted to be affixed to at least one molar on either side of the sheath adjacent the sheath fasteners and having a programmable locking mechanism to couple with the sheath fasteners and anchor the taste bud shield within the oral cavity for a predetermined period of time.

14. The taste bud shield of claim 13, wherein the form fitting flexible impermeable bio-compatible protective sheath is comprised of rubber.

15. The taste bus shield of claim 14, wherein the sheath fasteners are integrally formed with the sheath.

16. The taste bud shield of claim 15, wherein the mating fasteners are adapted to be removably affixed to a plurality of molars of the lower jaw on either side of the sheath and adjacent the sheath fasteners for removably anchoring the sheath within the oral cavity.

17. A method of preventing contact between food stuff and taste buds on a tongue comprising the steps of:

affixing mating fasteners to at least one molar on either side of the lower jaw;

inserting a tongue into a form fitting protective sheath extending from the apex to the root of the tongue completely covering the dorsal surface to at least the terminal sulcus, the ventral surface to at least the frenulum, and the side surfaces, the sheath having an inner and outer surface, the inner surface of the sheath directly overlaying the fungiform, foliate and circumvallate papillae, the sheath having at least one sheath fastener on either side and extending outwardly from its outer surface adjacent the mating fasteners; and coupling the corresponding mating and sheath fasteners to one another to anchor the protective sheath within the oral cavity.

18. The method of claim 17 further comprising the step of removably affixing the mating fasteners to a plurality of molars on either side of the sheath and adjacent the sheath fasteners.

19. The method of claim 17 further comprising affixing a programmable mating fastener to at least one molar on either side of the sheath and adjacent the sheath fasteners.

20. The method of claim 19 further comprising the step of programming the mating fasteners to couple with the sheath fasteners for a predetermined period of time.

21. A method of preventing contact between food stuff and taste buds on a tongue comprising the steps of:

affixing programmable mating fasteners to at least one molar on either side of the lower jaw;

inserting a tongue into a form fitting protective sheath extending from the apex to the root of the tongue completely covering the dorsal surface to at least the terminal sulcus, the ventral surface to at least the frenulum, and the side surfaces, the sheath having an inner and outer surface, the inner surface of the sheath directly overlaying the fungiform, foliate and circumvallate papillae, the sheath having at least one sheath fastener on either side and extending outwardly from its outer surface adjacent the mating fasteners;

programming the mating fasteners to couple with the sheath fasteners for a predetermined period of time; and coupling the corresponding mating and sheath fasteners to one another to anchor the protective sheath within the oral cavity for the predetermined period of time.

* * * * *